US011331264B2

(12) United States Patent
Legangneux et al.

(10) Patent No.: US 11,331,264 B2
(45) Date of Patent: May 17, 2022

(54) FERMENTED EXTRACT OF AERIAL PARTS OF BITTER ORANGE

(71) Applicant: CHANEL PARFUMS BEAUTE, Neuilly sur Seine (FR)

(72) Inventors: David Legangneux, Pantin (FR); Alix Toribio, Pantin (FR); François Lejeune, Pantin (FR); Emmanuelle Bouissou-Cadio, Pantin (FR); Gaëlle Gendronneau, Pantin (FR)

(73) Assignee: CHANEL PARFUMS BEAUTE, Neuilly sur Seine (FR)

(*) Notice: Subject to any disclaimer, the term of this patent is extended or adjusted under 35 U.S.C. 154(b) by 7 days.

(21) Appl. No.: 16/883,131

(22) Filed: May 26, 2020

(65) Prior Publication Data
US 2020/0375883 A1 Dec. 3, 2020

(30) Foreign Application Priority Data

May 28, 2019 (EP) .................................. 19305672

(51) Int. Cl.
*A61K 8/9789* (2017.01)
*A61K 36/752* (2006.01)
*A61Q 19/08* (2006.01)

(52) U.S. Cl.
CPC .......... *A61K 8/9789* (2017.08); *A61K 36/752* (2013.01); *A61K 2236/19* (2013.01); *A61K 2236/331* (2013.01); *A61K 2800/85* (2013.01); *A61Q 19/08* (2013.01)

(58) Field of Classification Search
CPC .... A61Q 19/08; A61Q 19/00; A61K 2236/00; A61K 2236/19; A61K 2800/85; A61K 36/752; A61K 8/9789; A61K 2236/331
See application file for complete search history.

(56) References Cited

U.S. PATENT DOCUMENTS 5,238,848 A * 8/1993 Hafner .............. C12R 2001/465
435/253.5

FOREIGN PATENT DOCUMENTS

| CN | 102743312 A | 10/2012 |
|---|---|---|
| CN | 108904398 A | 11/2018 |
| FR | 3032352 A1 | 8/2016 |
| KR | 1020130085012 A | 7/2013 |
| TW | 201010738 A | 3/2010 |

OTHER PUBLICATIONS

Karoui IJ, et al "Characterization of bioactive compounds in Tunisian bitter orange (*Citrus aurantium* L.) peel and juice and determination of their antioxidant activities" Biomed Res Int, 2013;2013:345415. doi: 10.1155/2013/345415. Epub Jun. 13, 2013. (Year: 2013).*
Lallemand Inc./Institut Œnologique de Champagne (IOC) "IOC Oct. 2007(TM)" Lallemand Wine Yeast Catalogue, 2 pages, Oct. 2016. (Year: 2016).*
Lallemand Inc./Institut Œnologique de Champagne (IOC) "IOC Divine(TM)" Lallemand Wine Yeast Catalogue, 1 page, ver 2.0, Jan. 2019. (Year: 2019).*
Lallemand Inc./Institut Œnologique de Champagne (IOC) "IOC FIZZ+(TM)" Lallemand Wine Yeast Catalogue, 1 page, ver 2.0, Jan. 2019. (Year: 2019).*
Azhdarzadeh F and Hojjati M "Chemical Composition and Antimicrobial Activity of Leaf, Ripe and Unripe Peel of Bitter Orange (*Citrus aurantium*) Essential Oils" Nutrition and Food Sciences Research, vol. 3 (No. 1; Jan.-Mar.), Jan. 2016, 3(1), pp. 43-50; DOI:10.18869/acadpub.nfsr.3.1.43. (Year: 2016).*
Extended European Search Report dated Nov. 29, 2019 in corresponding European Application No. 19305672.8; 14 pages.
Karoui, Iness Jabri et al., "Characterization of Bioactive Compounds in Tunisian Bitter Orange (*Citrus aurantium* L) Peel and Juice and Determination of Their Antioxidant Activities", Biomed Research International, vol. 2013, Jan. 1, 2013, pp. 1-12.
Kim, Sang Suk et al., "Phytochemical, antioxidant, and antibacterial activities of fermented Citrus unshiu byproduct", Food Science and Biotechnology, The Korea Soc. of Food Science and Technology, Heidelberg, vol. 26, No. 2, Apr. 30, 2017, pp. 461-466.
Yogaratnam 1 et al., "Production and optimization of bioethanol from sour orange (Citrus aurantium) peel using baker's yeast"; Proceedings of the Jaffna University International Research Conference; 2018; pp. 43-46.
Sarrou et al., "Volatile Constituents and Antioxidant Activity of Peel, Flowers and Leaf Oils of *Citrus aurantium* L. Growing in Greece"; Molecules: a Journal of Synthetic Chemistry and Natural Product Chemistry; Sep. 2, 2018 Vol. 18, No. 9; pp. 10639-10647.

* cited by examiner

*Primary Examiner* — Aaron J Kosar
(74) *Attorney, Agent, or Firm* — Maier & Maier, PLLC

(57) ABSTRACT

A fermented extract of aerial parts of *Citrus aurantium* and the process for obtaining it. The fermented extract may be added to a cosmetic composition. Also, the use of a fermented extract of *Citrus aurantium* to combat skin ageing, and also as an antioxidant active agent, to prevent/reduce oxidative stress and/or to detoxify the skin.

9 Claims, 2 Drawing Sheets

FERMENTED EXTRACT OF AERIAL PARTS OF BITTER ORANGE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD

The present invention concerns a fermented extract of aerial parts of bitter orange (*Citrus aurantium*), the process for obtaining it, a cosmetic or dermatological composition containing it and various cosmetic uses.

BACKGROUND

The skin is mainly made up of three layers, namely, starting from the most superficial, the epidermis, the dermis and the hypodermis.

The epidermis is in particular made up of keratinocytes (the majority), melanocytes (involved in skin pigmentation) and Langerhans cells. Its function is to protect the body from the external environment and to ensure its integrity, and in particular to slow down the penetration of microorganisms or chemical substances, and to prevent the evaporation of water contained in the skin.

To do this, the keratinocytes undergo a continuous process of oriented maturation during which the keratinocytes located in the basal layer of the epidermis form, at the terminal stage of their differentiation, corneocytes, which are dead cells totally keratinized in the form of cornified envelopes consisting of proteins and lipids such as ceramides. During this differentiation process, intercorneocyte epidermal lipids are additionally formed and then organized as bilayers (sheets) in the stratum corneum. Together with the aforementioned cornified envelopes, they participate in the barrier function of the epidermis.

As the skin ages, it becomes thinner, loses volume and elasticity and its barrier function is impaired.

The production of free radicals is one of the major factors in the acceleration of skin ageing. This production is mainly the result of exposure to UV rays, pollution and climatic variations. It leads to oxidative stress, which is the cause of the degradation of several constituent elements of the body, such as proteins, fatty acids, but also the DNA of the cells.

These free radicals can be neutralized by the action of antioxidants. One of the known ways of combating skin ageing is to apply cosmetic compositions containing such antioxidants to the skin.

Due to an ever-increasing willingness of consumers to turn to natural products containing as few synthetic ingredients as possible, and in view of the increasingly heavy regulatory constraints on compounds from the chemical industry, antioxidants from plant extracts are now favoured.

There is a real need for novel antioxidant molecules of plant origin that can effectively fight against skin ageing and the harmful effects of oxidative stress in general.

SUMMARY

The applicant has now demonstrated that an extract of aerial parts of bitter orange (*Citrus aurantium*) has remarkable antioxidant capacities. The particularity of this extract is that it is a fermented extract, i.e., obtained by an extraction process involving a fermentation step. As demonstrated in the present application, such an extract reduces the content of free radicals in cells by activating oxidative stress response pathways, in particular the nuclear factor erythroid-2-related factor 2 (NRF2) pathway.

Accordingly, in a first aspect, the present invention relates to a fermented extract of aerial parts of *Citrus aurantium*.

Such an extract is obtainable by an extraction process comprising a step of fermentation of an extract of aerial parts of *Citrus aurantium* with a yeast of the species *Saccharomyces cerevisiae*.

The present invention therefore also relates to a fermented extract of aerial parts of *Citrus aurantium* obtainable by a process comprising a step of fermentation of an extract of aerial parts of *Citrus aurantium* by a yeast belonging to the species *Saccharomyces cerevisiae*.

Another aspect of the invention relates to a cosmetic and/or dermatological composition comprising, in a physiologically acceptable medium, at least one fermented extract of *Citrus aurantium* as described above.

Finally, the invention also relates to the use of the extract described above to prevent/reduce skin ageing, but also to its use as an antioxidant active agent, to prevent/reduce oxidative stress and/or to detoxify the skin.

DETAILED DESCRIPTION

Figure 1:
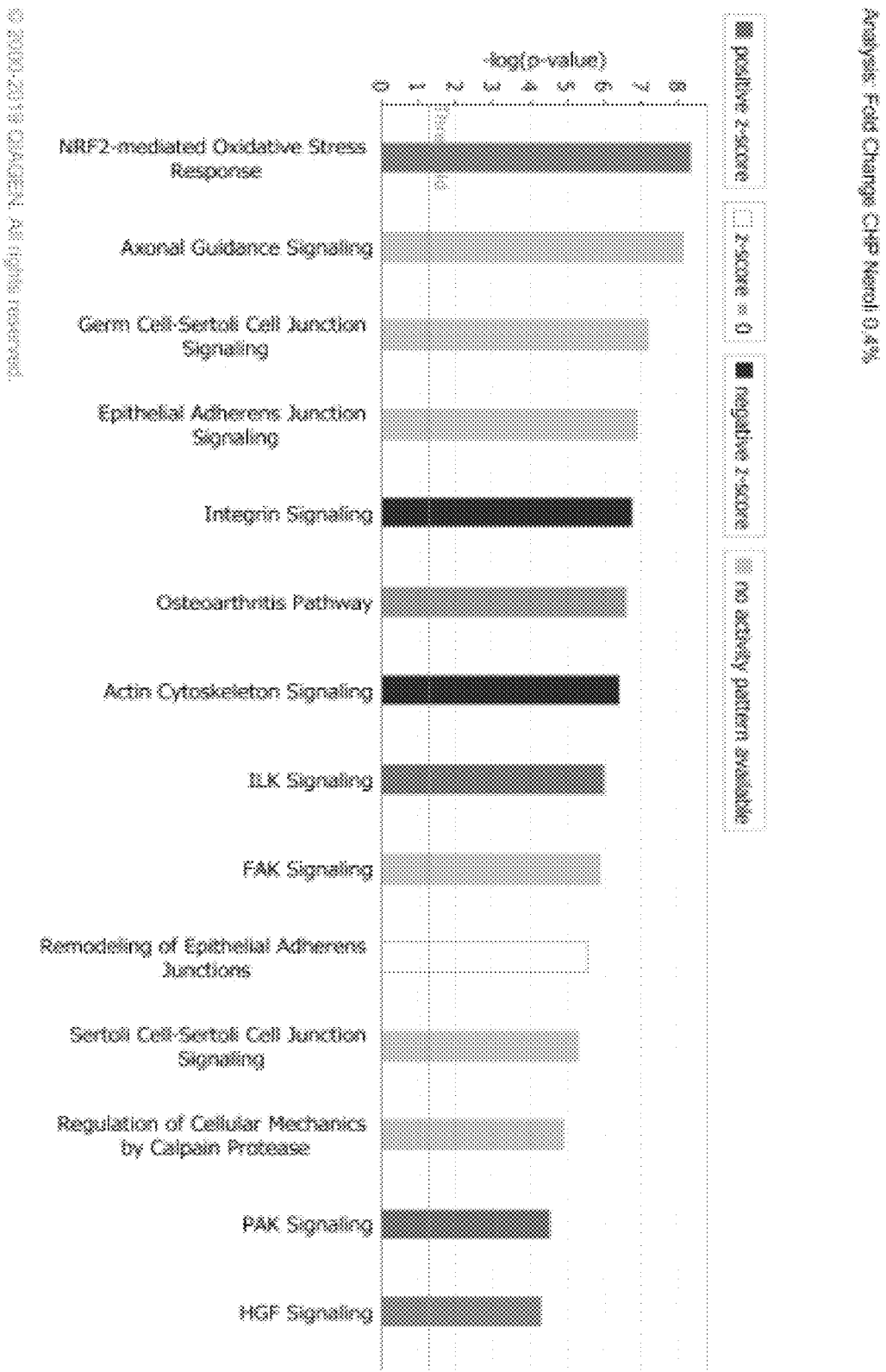
FIG. 1: Diagram showing the different biological pathways modulated in keratinocytes by a bitter orange extract according to the present invention.

According to a first aspect, the present invention relates to an extract of aerial parts of fermented *Citrus aurantium*. This extract is obtainable by a process comprising a step of fermentation of an extract of *Citrus aurantium* with a yeast belonging to the species *Saccharomyces cerevisiae*.

*Citrus aurantium*, commonly known as "bitter orange" or "*Bigaradia*" is a woody plant of the family Rutaceae. It is a thorny, evergreen tree, 3 to 10 metres tall, with fragrant flowers and edible fruits. The extract according to the present invention is an extract obtained from the aerial parts of *Citrus aurantium*, i.e. an extract obtained from flowers, leaves, fruits or twigs or from a mixture thereof. In a preferred embodiment, the extract is an extract from the flowers of *Citrus aurantium*, also called "orange blossoms".

The term "fermented" extract is used here to refer to an extract that has undergone a fermentation step. In the context of the present invention, this fermentation step is carried out with a yeast belonging to the species *Saccharomyces cerevisiae*.

Yeasts of the species *Saccharomyces cerevisiae* are well known and particularly used in the food industry, especially in the field of bread-making or for the fermentation of alcoholic beverages, for example in the field of oenology. The person skilled in the art knows how to obtain such yeasts to implement the present invention.

In a particular embodiment, said yeast belongs to the variety *Saccharomyces cerevisiae* var. *bayanus*. According to this embodiment, the yeast can be selected from the yeast strains marketed under the tradenames IOC FIZZ+, IOC DIVINE, IOC 18-2007 or a mixture thereof. All these strains are listed by the Institut Français de la Vigne et du Vin [French Institute in Vine and Wine] and are easily accessible to the skilled person.

The *Saccharomyces cerevisiae* var. *bayanus* strain sold under the tradename IOC FIZZ+ is a mixture of two yeasts deposited at the Institut Pasteur under the number LYCC 6022: LA CLAIRE CGC62 and LYCC 6039: LA CLAIRE SP665.

The *Saccharomyces cerevisiae* var. *bayanus* strain sold under the tradename IOC DIVINE corresponds to the strain deposited at the Institut Pasteur under the number LYCC 7000, and the *Saccharomyces cerevisiae* var. *bayanus* strain sold under the tradename IOC 18-2007 to the strain deposited at the Institut Pasteur under the number CNCM I-5320.

The yeast strains used in the context of the present invention may be in dry form, in liquid form or in the form of yeast cream.

In a particular embodiment, the *Saccharomyces cerevisiae* strain is in dry form.

Typically, the fermentation step is carried out using the *Saccharomyces cerevisiae* strain at between 1 and 5% by mass relative to the solution to be fermented, particularly at between 2 and 3% by mass relative to the solution to be fermented, and more particularly at 2% by mass relative to the solution to be fermented.

In a particular embodiment, the fermentation step can be carried out by means of a leaven. This leaven is prepared from a concentrated *Citrus aurantium* extract fermented with the *Saccharomyces cerevisiae* strain. The extract used for the leaven is typically concentrated to a dry matter content of 5 to 30%.

According to this embodiment, the fermentation step is carried out by adding this leaven to the *Citrus aurantium* extract. The use of a leaven starts the fermentation and thus improves the kinetics of the fermentation step.

Typically, the leaven is prepared by fermenting for about 2 hours at room temperature (or alternatively at 37° C.) a *Citrus aurantium* extract concentrated to between 5 and 50%, particularly to between 15 and 30% dry matter in water with 10% by weight of *Saccharomyces cerevisiae* dry yeast. 1 to 5% of this leaven by weight, preferentially 2% of leaven by weight, is added to the *Citrus aurantium* extract for the fermentation step.

The *Citrus aurantium* extract used to obtain the fermented extract according to the invention may be obtained by any extraction process known to the person skilled in the art.

Typically, a process for the preparation of a plant extract comprises the following steps:
 a) extraction of the plant (in the present case the aerial parts of *Citrus aurantium*) with at least one alcoholic solvent and/or water;
 b) filtration, for example by sieving, of the mixture obtained in a) in order to remove plant residues,
 c) optionally, decolourization of the mixture obtained in step b); and
 d) removal of the solvent and concentration of the extract.

In order to obtain the fermented extract of *Citrus aurantium* according to the present invention, a step e) is typically added after steps a) to d) above, this step e) comprising the fermentation of the extract obtained from step d) with a yeast belonging to the species *Saccharomyces cerevisiae*.

Step a) may further include crushing the plant, typically its flowers and/or leaves, to obtain a particle size of less than 5 cm, preferably less than 2 cm.

The extraction step is carried out with at least one extraction solvent consisting of an alcoholic solvent and/or water. The typical plant to solvent ratio is 1 to 10 (weight/weight).

In a particular embodiment, the alcoholic solvent is 96° ethanol.

The extraction solvent may contain 0 to 100% by volume of water and 0 to 100% by volume of alcoholic solvent. In a particular embodiment, the extraction solvent comprises 100% water, in another embodiment it comprises 100% ethanol. The extraction solvent can also comprise 50% by volume of water and 50% by volume of ethanol.

In a particular embodiment, the water can be deionized water. In the present invention, the extraction solvent is typically deionized water.

The extraction step lasts at least 1 hour, preferably at least 2 hours, particularly at least 3 hours, and can be repeated once or twice.

As indicated above, the extraction process may include a step in which the mixture from step b) is decolourized. The purpose of this step is to remove pigments present in the extract such as chlorophylls and xanthophylls. The person skilled in the art is familiar with several methods of removing these pigments. Decolourization can, for example, be carried out by bringing the mixture into contact with activated carbon. After decolourization, the mixture is filtered to remove the carbon residue.

Typically, step d) involves concentrating the extract to a dry matter to water ratio in the range of 5 to 30%, preferably 15% to 30%.

This concentration step is typically performed by evaporation of the extraction solvent (alcoholic solvent and/or water). This extraction can for example be done under vacuum.

The *Citrus aurantium* extract from step d), i.e. the concentrated *Citrus aurantium* extract, can be used to prepare the above mentioned leaven.

The process described above may further include a step d') between steps d) and e), in which the mixture containing the concentrated extract is finely filtered (typically at 2 µm or even 0.2 µm) to remove fine particles and residual bacteria.

The process may further include a step f), in which the fermented extract is filtered and then diluted to obtain an extract containing 1 to 15% dry matter by weight, particularly about 10% dry matter by weight. This extract may be in the form of a clear and stable aqueous solution.

In a particular embodiment, the process for obtaining the fermented extract of *Citrus aurantium* according to the present invention comprises the following steps:
 a) An orange blossom powder ground to a fineness of less than 2 cm is extracted twice with deionized water at 75° C., for a minimum of 2 hours, the plant/solvent ratio is 1 to 10 (weight/weight);
 b) The mixture is filtered to 4 µm;
 c) The resulting mixture is subjected to decolourization by contact with activated carbon for one hour and then undergoes microfiltration to 1 µm in order to remove the carbon residues;
 d) The extract is concentrated by removing part of the water by vacuum evaporation until a dry matter content close to 15% (weight/weight) is reached;
 d') The mixture is filtered at 0.2 µm;
 e) Fermentation for 24 to 48 hours at 37° C. of the mixture with 2% by weight of a leaven, said leaven having been obtained by concentrating part of the extract obtained before step d) to 30% dry matter in water and adding 10% by weight of dry *Saccharomyces cerevisiae* yeast for a first fermentation for 2 hours at 37° C.;

f) The fermented extract is then filtered at 1 μm, then diluted to obtain an extract containing 1 to 10% dry matter by weight to which is added 0.7% phenoxyethanol or 20% 1,3-propanediol (10% dry matter/70% water, weight/weight ratio) for better preservation.

The fermented extract according to the present invention has remarkable antioxidant properties. As demonstrated in the examples below (see especially Examples 2 and 3), it significantly reduces oxidative stress in skin cells such as keratinocytes. In particular, it activates the nuclear factor erythroid-2-related factor 2 (NRF2) pathway, which is known to be a response pathway to oxidative stress. NRF2 is a transcription factor which, through its binding to the regulatory sequence known as the antioxidant response element (ARE), will allow the expression of genes coding for antioxidant enzymes. The activation of this pathway therefore has the effect of reducing the free radical content of tissues through the action of antioxidant agents.

As explained above, the production of free radicals, and the oxidative stress that this production generates, is one of the major factors in the acceleration of skin ageing. The reduction of free radicals, and therefore of oxidative stress, fights against the signs of skin ageing such as wrinkles and fine lines, loss of firmness and elasticity due to tissue loss in the epidermis and/or dermis; the loss of radiance due to reduced microcirculation and a slowdown in cell renewal in the epidermis, the appearance of pigmentation spots associated with a malfunction in melanin synthesis, or skin dryness resulting from a reduction in the barrier function of the stratum corneum and a slowdown in epidermal renewal.

Thus according to another aspect, the present invention relates to the use of a fermented extract of aerial parts of *Citrus aurantium* to prevent/reduce skin ageing.

The invention also relates to the use of a fermented extract of aerial parts of *Citrus aurantium* as an antioxidant active agent and/or to prevent/reduce oxidative stress and/or to detoxify the skin.

An "antioxidant" active agent is a compound with anti-free radical properties, i.e. with the capacity to neutralise free radicals, and in particular the oxidation reactions linked to these free radicals. This neutralization leads to a reduction in the content of free radicals in the tissues.

"Oxidative stress" is an imbalance between the excessive amount of free radicals and antioxidants in the tissues. The neutralization of free radicals by the supply of antioxidant active agents therefore helps to reduce this oxidative stress. Example 3 below shows a way to measure oxidative stress and in particular the effect of an antioxidant active agent on this oxidative stress.

The reduction of free radicals and oxidative stress in the skin helps to "detoxify" the skin, i.e. to obtain a "detoxifying" effect. The term "detoxifying" means an effect that fights the harmful effects of free radicals on the skin.

The extract according to the present invention can advantageously be incorporated in a cosmetic or dermatological composition. Therefore, according to another aspect, the present invention relates to a cosmetic or dermatological composition comprising, in a cosmetically or pharmaceutically acceptable vehicle, an alcoholic extract of *Citrus aurantium* parts according to the invention.

Preferably, said extract is present in the cosmetic or dermatological composition in a proportion of 0.001 to 10% by total weight of the composition, in particular in a proportion of 0.01 to 10%, preferably 0.1 to 10% by total weight of the composition. Said cosmetic or dermatological composition may in particular be suitable for topical application.

Advantageously, said cosmetic or dermatological composition may be in the form of a powder, an emulsion, a microemulsion, a nanoemulsion, a suspension, a solution, a lotion, a cream, an aqueous or hydroalcoholic gel, a foam, a serum, a solution or a dispersion for aerosol, or a dispersion of lipid vesicles.

In the case of an emulsion, it can be a water-in-oil or oil-in-water emulsion.

The cosmetic or dermatological composition according to the invention may also include a solvent chosen according to the various ingredients and the form of administration.

Examples include water (preferably demineralized water), an alcohol such as ethanol, or a diethylene glycol ether such as ethoxydiglycol or diethylene glycol monomethyl ether.

Said cosmetic composition may also comprise, in addition to the extract according to the invention, at least one additive usual in the field, such as for example at least one compound chosen from an emollient or humectant agent, a gelling and/or thickening agent, a surfactant, an oil, an active agent, a dye, a preservative, an antioxidant agent, an active agent, an organic or inorganic powder, a sunscreen and a fragrance.

In particular, said composition may contain:

One or more emollient or humectant agent(s), which may be selected for example from glycerine, glycols, water-soluble silicones such as that sold under the name KF6011 (Shin Etsu) and water-soluble jojoba, such as that sold under the name Resplanta Jojoba (Res Pharma).

Said emollient or humectant agent may be present in the composition at a content in the range of 0 to 30%, preferably to 10% by weight, relative to the total weight of the composition.

One or more gelling and/or thickening agent(s) for the aqueous phase, chosen for example from cellulosic derivatives, gums of plant origin (guar, locust bean, alginates, carrageenans, pectin), of microbial origin (xanthan), clays (laponite), materials identified by the INCI names "ammonium acryloyldimethyltaurate/vp copolymer" and "ammonium acryloyldimethyl-taurate/beheneth-25 methacrylate copolymer" (such as those sold under the names Aristoflex AVC and HMB by Clariant).

Said gelling and/or thickening agent may be present in the composition at a content in the range of 0 to 10% by weight, relative to the total weight of the composition.

One or more surfactant(s), preferably nonionic, present in a content in the range of 0 to 8%, preferably 0.5 to 3% by weight, relative to the total weight of the composition.

One or more room-temperature liquid fats, commonly known as oil(s), volatile or non-volatile, hydrocarbon or silicone, linear, cyclic or branched, for example isododecane, cyclopentadimethylsiloxane, dimethicones, isononyl isononanoate or pentaerythrityl tetraisostearate, preferably in an amount of 0 to about 10%, preferably 0.5 to 5% by weight, relative to the total weight of the composition.

One or more active agent(s), of natural or synthetic origin, having biological activity, for example selected from vitamins, trace elements, allantoin, plant proteins, plant extracts, moisturizing agents, anti-ageing agents, antioxidants, shine enhancers and mixtures thereof. In particular, the active agent is selected from *Vanilla*

*planifolia* fruit water, niacinamide, hyaluronic acid and its derivatives, a yeast extract and mixtures thereof.

One or more water-soluble dye(s) such as, for example, ponceau disodium salt, alizarin green disodium salt, quinoline yellow, amaranth trisodium salt, tartrazine disodium salt, rhodamine monosodium salt, fuchsin or xanthophyll disodium salt, preferably in an amount of 0 to about 2% by weight, relative to the total weight of the composition.

Other additives commonly used in cosmetics may also be present in the composition according to the invention, such as preservatives, antioxidants or fragrances well known in the technical field.

The skilled person is able to choose, from among all these possible additives, both the nature and the amount of those to be added to the composition, so that it retains all its properties.

The invention will now be illustrated by the following non-limiting examples.

EXAMPLES

Example 1—Process for the Extraction of Bitter Orange According to the Present Invention 1) Dried orange blossom flowers are crushed to a fineness of less than 2 cm;
2) The orange blossom powder is then extracted twice with deionized water at 75° C., for a minimum of 2 hours, the plant/solvent ratio is 1 to 10 (weight/weight);
3) The mixture is sieved at 100 µm in order to remove plant residues, then left to rest overnight and filtered again to 4 µm;
4) The resulting mixture is subjected to decolourization by contact with activated carbon for one hour to remove pigments such as chlorophylls and xanthophylls;
5) The decolourized mixture is separated from the carbon residue by means of microfiltration (to 1 µm);
6) The extract is concentrated by removing part of the water by vacuum evaporation until a dry matter content close to 15% (weight/weight) is reached;
7) The mixture is filtered at 0.2 µm to remove fine particles and residual bacteria;
8) In order to prepare the leaven for the fermentation of the extract, part of the extract obtained before step 6) is concentrated to 30% dry matter in water and then 10% by weight of dry yeast *Saccharomyces cerevisiae* var. *bayanus* is added. The mixture is stirred for 2 hours at room temperature. This mixture constitutes the leaven.
9) 2% leaven by weight is added to the mixture from step 6);
10) After 24 to 48 hours of fermentation at room temperature with stirring and in the dark, the fermented extract is left to settle overnight to remove the gas bubbles formed;
11) The fermented extract is then filtered at 1 µm, then diluted to obtain an extract containing 10% dry matter, 0.7% phenoxyethanol is added for better preservation or 20% 1,3-propanediol (10% dry matter/70% water, weight/weight ratio) and the whole is filtered at 0.2 µm.

The contents of the orange blossom extract are given in Table 1 below.

TABLE 1

Composition of an extract of bitter orange obtained by the process of the invention

| Molecular family | Molecules | Conventional extract | Fermented extract |
|---|---|---|---|
| Saccharides | Fructose, Glucose, Sucrose | 2.20% | 0.00% |
| Organic and other acids | Synephrine, Stachydrine, Quinic Acid, Malic Acid | 1.24% | 1.32% |
| Flavonoids | Neoeriocitrin, Narirutin, Naringin, Hesperetin glucoside, Hesperidin, Neohesperidin | 2.43% | 4.40% |
| Others | Others | 4.13% | 4.64% |

As demonstrated above, the process according to the present invention completely removes simple sugars from an orange blossom extract. The process according to the invention also increases the polyphenol content of the extract.

Example 2—Activation of the Oxidative Stress Response Pathway in Normal Human Keratinocytes Treated with Bitter Orange Extract According to the Present Invention Protocol:

Normal human epidermal keratinocytes from three different donors (aged 19 to 30 years) were inoculated in 24-well plates and cultured in SFM-complemented keratinocyte medium for 48 h at 37° C., 5% $CO_2$. The cells were then incubated or not (control) with 0.4% bitter orange extract for 24 h. The conditions were carried out with n=2. At the end of the incubation, the culture supernatants were removed and the cell monolayers rinsed with PBS. Total RNA was extracted using Tripure® Isolation Reagent according to the supplier's recommendations. The quantity and quality of the RNAs were evaluated by capillary electrophoresis (2100 Bioanalyzer, Agilent). Complementary DNA was synthesized and a transcriptome was produced on an Affymetrix GeneChip Human Transcriptome Array 2.0. Bioinformatics analysis of genes whose expression is modulated by at least a factor of 2 was performed using Ingenuity Pathway Analysis software (IPA®, Qiagen). This software collects information on molecule-to-molecule interactions, biological networks and canonical pathways in the Ingenuity Knowledge database.

Results:

The biological pathways modulated by bitter orange extract are shown in FIG. 1. The major cellular function that is activated by the bitter orange extract in keratinocytes is the NRF2 pathway of response to oxidative stress with 31 genes involved. The list of genes overexpressed in this biological pathway is presented in Table 1.

| © 2000-2018 QIAGEN. All rights reserved. | | |
|---|---|---|
| Symbol | Entrez Gene Name | Expr Fold Change |
| GCLC | glutamate-cysteine ligase catalytic subunit | 8.330 |
| GPX2 | glutathione peroxidase 2 | 5.240 |

© 2000-2018 QIAGEN. All rights reserved.

| Symbol | Entrez Gene Name | Expr Fold Change |
|---|---|---|
| MGST1 | microsomal glutathione S-transferase 1 | 5.210 |
| NQO1 | NAD(P)H quinone dehydrogenase 1 | 5.120 |
| ABCC2 | ATP binding cassette subfamily C member 2 | 4.510 |
| PIK3C2B | phosphatidylinositol-4-phosphate 3-kinase catalytic subunit type 2 beta | 4.140 |
| GSR | glutathione-disulfide reductase | 3.690 |
| ABCC1 | ATP binding cassette subfamily C member 1 | 3.210 |
| CBR1 | carbonyl reductase 1 | 3.030 |
| TXNRD1 | thioredoxin reductase 1 | 2.840 |
| GSTM3 | glutathione S-transferase mu 3 | 2.830 |
| GSTA4 | glutathione S-transferase alpha 4 | 2.800 |
| FTH1 | ferritin heavy chain 1 | 2.780 |
| SOD2 | superoxide dismutase 2 | 2.750 |
| DNAJB1 | DnaJ heat shock protein family (Hsp40) member Bl | 2.590 |
| EPHX1 | epoxide hydrolase 1 | 2.490 |
| GSTM4 | glutathione S-transferase mu 4 | 2.400 |
| DNAJC3 | DnaJ heat shock protein family (Hsp40) member C3 | 2.380 |
| HSPB8 | heat shock protein family B (small) member 8 | 2.370 |
| GCLM | glutamate-cysteine ligase modifier subunit | 2.270 |
| PRDX1 | peroxiredoxin 1 | 2.230 |
| FKBP5 | FK506 binding protein 5 | 2.200 |
| FTL | ferritin light chain | 2.190 |
| TXN | thioredoxin | 2.070 |

Example 3: Reduction of Oxidative Stress in Normal Human Keratinocytes Treated with Bitter Orange Extract According to the Present Invention Protocol:

Normal human epidermal keratinocytes from a 27-year-old donor were seeded in 6-well plates and cultured for 72 h at 37° C., 5% $CO_2$. The cells were then incubated or not (control) with 0.4% bitter orange extract for 24 h before oxidative stress was induced by treatment of the cells with 50 µM menadione sodium bisulphite (Sigma). Oxidative stress is observed using a MitoSOX Red Mitochondrial Superoxide Indicator (Life technologies) fluorescent probe. Photographs of the cultures were taken 1.5 h after the stress and the intensity of the fluorescent signal was quantified.

Figure 2:
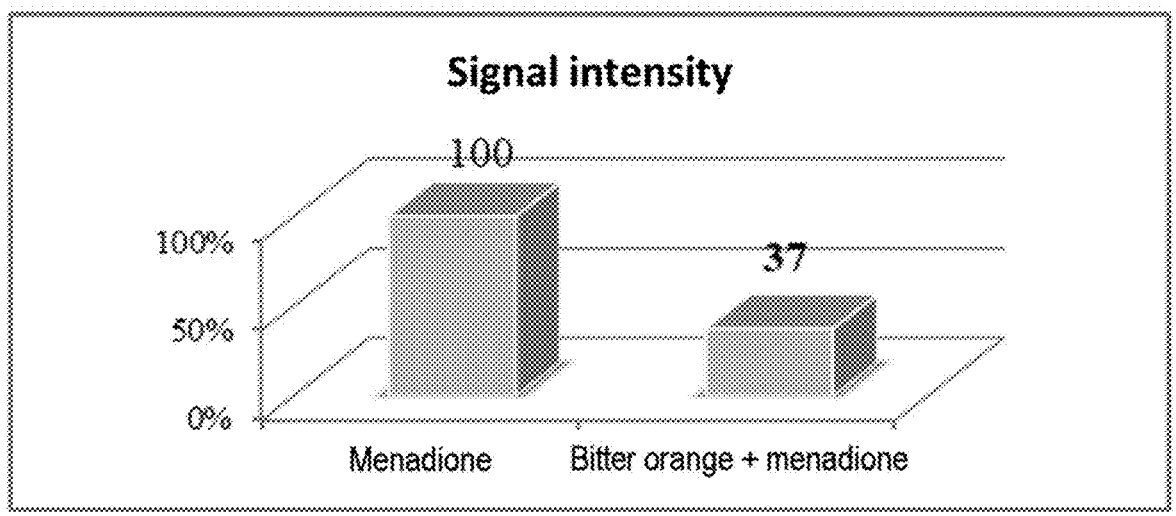
FIG. 2: Reduction of oxidative stress in keratinocytes after treatment with a bitter orange extract according to the present invention.

Results:

A 63% decrease in signal intensity was observed after treatment with the bitter orange extract compared with the control condition (FIG. 2).

Example 4: Cosmetic Composition

The following compositions can be prepared in a traditional way for skilled person. The amounts indicated below are expressed in weight percentages. Ingredients in capital letters are identified in accordance with the INCI designation.

| 4A - oil/water emulsion INCI name | (% W/W) |
|---|---|
| Jojoba esters | 1-10 |
| Limnanthes alba (meadowfoam) seed oil | 1-10 |
| Undecane & tridecane & tocopherol & helianthus annuus (sunflower) seed oil | 1-10 |
| Butyrospermum parkii butter (LIPEX SHEASOFT) | 1-10 |
| Camellia kissi seed oil | 1-10 |
| Butyrospermum parkii butter extract (LIPEX SHEA TRIS) | 1-10 |
| Cetyl ethylhexanoate | 1-5 |
| Diisostearyl dimer dilinoleate (SCHERCEMOL DISD) | 1-10 |
| Sodium acrylates copolymer & lecithin | 0.1-5 |
| Amodimethicone | 0.1-2 |
| Glyceryl stearate & PEG-100 stearate | 0.1-5 |
| CARBOMER | 0.01-5 |
| Alcaligenes polysaccharides | 1-10 |
| Silica | 0.1-10 |
| Sodium hyaluronate | 0.01-3 |
| Glycerine | 1-30 |
| Polyquaternium-51 | 1-10 |
| Adenosine | 0.1-0.5 |
| Niacinamide | 0.1-5 |
| Palmitoyl Tripeptide-1 & Palmitoyl Tetrapeptide-7 | 1-5 |
| Secale Cereale (Rye) Seed Extract | 1-5 |
| Extract according to the invention | 0.001-10 |
| Ascorbyl glucoside | 0.001-5 |
| Glycol | 0,1-10 |
| Glycols (Caprylyl Glycol and/or Pentylene and/or Butylene Glycol and/or propanediol) | |
| Water | Qs 100 |

| 4b - oil/water INCI name | cream emulsion (% w/w) |
|---|---|
| Behenyl alcohol | 1-5 |
| Cetyl alcohol | 0.1-5 |
| Phenyl trimethicone | 1-5 |
| Dimethicone & Dimethicone/Vinyl Dimethicone Crosspolymer | 1-30 |
| Ectoin | 0.1-5 |
| PPG-2 myristyl ether propionate | 1-10 |
| Titanium Dioxide | 1-20 |
| Zinc Dioxide | 1-20 |
| Diethylamino Hydroxybenzoyl Hexyl Benzoate (Uvinul A+) | 1-5 |
| Bis-Ethylhexyloxyphenol Methoxyphenyl Triazine (Tinosorb S) | 1-5 |
| (Tinosorb M) | 1-5 |
| Ethyl hexyl Methoxycinnamate | 1-7.5 |
| Polysilicone -11 | 1-5 |
| Silica | 1-5 |
| lauroyl lysine | 1-5 |
| 020-22 alkyl phosphate & 020-22 alcohols | 0.5-5 |
| Glyceryl stearate & PEG-100 stearate | 0.5-5 |
| Sodium acrylate/sodium acryloyldimethyltaurate copolymer | 0.1-5 |
| Hydrogenated starch hydrolysate & maltooligosyl glucoside | 0.1-10 |
| Xanthan Gum | 0,01-2 |
| Agar | 0.1-5 |
| Adenosine | 0.1-0.5 |
| Niacinamide | 0.1-5 |
| Secale cereale (rye) seed extract | 0.1-5 |
| Palmitoyl tetrapeptide-7 | 1-5 |
| Vanilla planifolia fruit water | 0.1-2 |
| Vanilla planifolia flower extract | 0.1-2 |
| Yeast extract | 1-3 |
| Saccharide isomerate | 1-5 |
| Extract according to the invention | 0.001-10 |
| Licorice extract | 0.001-5 |
| Water | Qs 100 |

These compositions can be applied daily, morning and/or evening, to the skin.

The invention claimed is:

1. An extract of aerial parts of *Citrus aurantium*, wherein said extract is in a form and effective amount suitable for cosmetic and/or dermatological use.

2. The extract according to claim 1, wherein said *Citrus aurantium* extract is a flower extract.

3. A cosmetic composition comprising an extract of *Citrus aurantium* according to claim 1.

4. A cosmetic method comprising the administration, to a patient in need thereof, of an effective amount of the extract according claim 1 as an antioxidant active agent and/or to prevent/reduce oxidative stress and/or to detoxify the skin.

5. A cosmetic method for preventing/reducing skin ageing comprising the administration of an effective amount of the extract according to claim 1 to a subject in need thereof.

6. The extract according to claim 1, wherein said extract is obtained by a process comprising a step of fermentation of an extract of aerial parts of *Citrus aurantium* with a yeast belonging to the species *Saccharomyces cerevisiae*.

7. The extract according to claim 6, wherein said yeast of the species *Saccharomyces cerevisiae* is of the variety *Saccharomyces cerevisiae* var. *bayanus*.

8. A process for obtaining a fermented extract of aerial parts of *Citrus aurantium* in a form and effective amount suitable for cosmetic and/or dermatological use, said process comprising the following steps:
   a) extraction of aerial parts of *Citrus aurantium* with at least one alcoholic solvent and/or water;
   b) filtration of the mixture obtained in a) in order to remove plant residues;
   c) optionally, decolourization of the mixture obtained from step b);
   d) removal of the extraction solvent and concentration of the resulting extract; and
   e) fermentation of the extract obtained from *Citrus aurantium* by a yeast belonging to the species *Saccharomyces cerevisiae*.

9. The process according to claim 8, wherein the fermentation step is carried out by means of a leaven prepared from the fermentation of a concentrated *Citrus aurantium* extract with the strain of *Saccharomyces cerevisiae*.

* * * * *